United States Patent
Moinet et al.

(10) Patent No.: US 8,791,115 B2
(45) Date of Patent: Jul. 29, 2014

(54) COMBINATION OF TRIAZINE DERIVATIVES AND INSULIN SENSITISERS

(75) Inventors: Gérard Moinet, Orsay (FR); Daniel Cravo, Sartrouville (FR); Didier Mesangeau, Combs la Ville (FR)

(73) Assignee: Poxel SAS, Lyons (FR)

( * ) Notice: Subject to any disclaimer, the term of this patent is extended or adjusted under 35 U.S.C. 154(b) by 679 days.

(21) Appl. No.: 12/160,664

(22) PCT Filed: Dec. 18, 2006

(86) PCT No.: PCT/EP2006/012185
§ 371 (c)(1),
(2), (4) Date: Jul. 11, 2008

(87) PCT Pub. No.: WO2007/079917
PCT Pub. Date: Jul. 19, 2007

(65) Prior Publication Data
US 2010/0285117 A1    Nov. 11, 2010

(30) Foreign Application Priority Data
Jan. 13, 2006    (FR) .................... 06 00344

(51) Int. Cl.
*A61K 31/53* (2006.01)
*A61K 31/155* (2006.01)

(52) U.S. Cl.
USPC ........... 514/243; 514/245; 514/246; 514/636; 514/866

(58) Field of Classification Search
USPC .................. 514/243, 245, 246, 636, 866
See application file for complete search history.

(56) References Cited

U.S. PATENT DOCUMENTS

| | | | |
|---|---|---|---|
| 5,885,980 | A | 3/1999 | Gutierrez et al. |
| 6,011,049 | A | 1/2000 | Whitcomb |
| 2005/0037981 | A1 | 2/2005 | Beavers et al. |
| 2008/0108619 | A1 | 5/2008 | Moinet et al. |

FOREIGN PATENT DOCUMENTS

| | | |
|---|---|---|
| WO | WO-00 27401 | 5/2000 |
| WO | WO 01/21602 | 9/2000 |
| WO | WO 01/35941 | 11/2000 |
| WO | WO 01/55122 A | 8/2001 |
| WO | WO 01/82867 A2 | 11/2001 |
| WO | WO 2004/089917 A2 | 10/2004 |
| WO | WO 2005/065663 A | 7/2005 |

OTHER PUBLICATIONS

Setter SM. et al. "Metformin Hydrochloride in the Treatment of Type 2 Diabetes Mellitus: A Clinical Review with a Focus on Dual Therapy". Clinical Therapeutics, vol. 25, No. 12, 2003, pp. 2991-3026.*
International Search Report completed Mar. 27, 2007 in International Patent Application No. PCT/EP2006/012185 filed Dec. 18, 2006.
O'Moore-Sullivan and Prins, "Thiazolidinediones and type 2 diabetes: new drugs for an old disease", Med. J. Aust. Apr. 15, 2002, vol. 176, pp. 381-386).
Trisha M O'Moore-Sullivan et al., "Thiazolidinediones and type 2 diabetes: new drugs for an old disease", MJA—vol. 176 Apr. 15, 2002, pp. 381-386.

* cited by examiner

*Primary Examiner* — Renee Claytor
(74) *Attorney, Agent, or Firm* — Millen, White, Zelano & Branigan, P.C.

(57) ABSTRACT

The present invention relates to combinations of triazine derivatives and of insulin sensitizers.

20 Claims, No Drawings

COMBINATION OF TRIAZINE DERIVATIVES AND INSULIN SENSITISERS

FIELD OF THE INVENTION

The present invention relates to a pharmaceutical composition of triazine derivatives or described pharmaceutically acceptable salts thereof with an insulin sensitiser, for the manufacture of a medicament that can be used in the treatment of non-insulin-dependent diabetes and pathologies associated with insulin resistance syndrome.

TECHNICAL BACKGROUND

"Diabetes mellitus" (or diabetes) is one of the most prevalent diseases in the world today. Individuals suffering from diabetes have been divided into two classes, namely type I or insulin-dependent diabetes mellitus and type II or non-insulin-dependent diabetes mellitus (NIDDM). Non-insulin-dependent diabetes mellitus (NIDDM) accounts for approximately 90% of all diabetics, and is estimated to affect 12 to 14 million adults in the United States alone (6.6% of the population). NIDDM is characterised both by fasting hyperglycaemia and exaggerated postprandial increases in plasmatic glucose levels. NIDDM is associated with a variety of long-term complications, including microvascular diseases, such as retinopathy, nephropathy and neuropathy, and macrovascular diseases, such as coronary heart disease. Numerous studies in animal models show a causal relationship between long-term complications and hyperglycaemia. Recent results obtained by the Diabetes Control and Complications Trial (DCCT) and the Stockholm Prospective Study have for the first time demonstrated this relationship in man by showing that insulin-dependent diabetics have a substantially lower risk of development and progression of these complications if they are subjected to tighter glycaemic control. Tighter control is also expected to benefit NIDDM patients.

Hyperglycaemia in the case of NIDDM is associated with two biochemical anomalies, namely insulin resistance and insufficiency of insulin secretion.

The initial treatment of NIDDM is based on a controlled diet and controlled physical exercise, since a considerable number of diabetics are overweight or obese (~67%) and since loss of weight can improve insulin secretion and sensitivity to insulin and lead to normal glycaemia.

Patients suffering from a hyperglycaemia that cannot be controlled solely by a diet and/or physical exercise are then treated with oral antidiabetics.

A number of categories of oral antidiabetics are currently used in monotherapy for the treatment of NIDDM:
  insulin secretion stimulators. They are represented, firstly, by sulfonylureas (SU) and by "glinides". As regards SUs, mention will be made in particular of carbutamide (Glucidoral®), glibenclamide/glyburide (Daonil®, Euglucan®), glibomuride (Glutril®), gliclazide (Diamicron®), glimepiride (Amarel®) and glipizide (Glibenese®). As regards the "glinides", mention will be made in particular of repaglinide (NovoNorm®);
  agents that reduce glucogenesis, represented by the biguanides. Mention will be made in particular of metformin (Glucophage®, Stagid®);
  insulin sensitisers, represented mainly by thiazolidinediones (TZD). Mention will be made in particular of pioglitazone (Actos®) and rosiglitazone (Avandia®);
  alpha-glucosidase inhibitors. Mention will be made in particular of acarbose (Glucor®) and miglitol (Diastabol®).

However, the monotherapy may show a loss of efficacy over time. This is referred to as "secondary deficiency". This may represent up to 50% unsatisfactory response after 10 years of treatment. The studies conducted have shown that it is possible to deal with this problem by combining in the same pharmaceutical form metformin with TZDs (EP 869 796 B1 or EP 861 666 B1).

Moreover, the combination metformin+rosiglitazone (Avandamet®) has been marketed.

However, these metformin-based combinations have adverse effects associated with the use of metformin, in particular intestinal symptoms, such as nausea, diarrhea and abdominal pain. Triazine derivatives with an antidiabetic effect comparable to metformin have been described in WO 01/55122. However, their combination has never been suggested.

The applicant has developed a novel pharmaceutical composition comprising an antidiabetic agent of triazine type, such as those described in WO 01/55122 and an insulin sensitiser.

Unexpectedly, the combinations according to the invention show synergistic activity and significantly reduce the side effects of the known combinations.

DESCRIPTION OF THE INVENTION

The present invention relates to a novel pharmaceutical composition comprising an insulin sensitiser and a compound of the general formula (I):

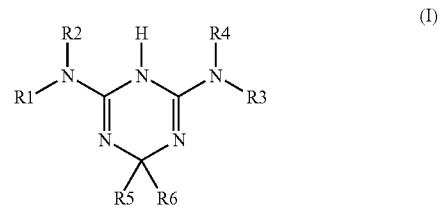

in which:
R1, R2, R3 and R4 are independently chosen from the following groups:
  H,
  (C1-C20)alkyl optionally substituted by halogen, (C1-C5) alkyl, (C1-C5)-alkoxy or (C3-C8)cycloalkyl,
  (C2-C20)alkenyl optionally substituted by halogen, (C1-C5)alkyl or (C1-C5)alkoxy
  (C2-C20)alkynyl optionally substituted by halogen, (C1-C5)alkyl or (C1-C5)alkoxy
  (C3-C8)cycloalkyl optionally substituted by (C1-C5)alkyl or (C1-C5)-alkoxy
  hetero(C3-C8)cycloalkyl bearing one or more heteroatoms chosen from N, O and S and optionally substituted by (C1-C5)alkyl or (C1-C5)alkoxy
  (C6-C14)aryl(C1-C20)alkyl optionally substituted by amino, hydroxyl, thio, halogen, (C1-C5)alkyl, (C1-C5) alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
  (C6-C14)aryl optionally substituted by amino, hydroxyl, thio, halogen, (C1-C5)alkyl, (C1-C5)alkoxy, (C1-C5) alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl,
  (C1-C13)heteroaryl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl, R1 and R2, on the one hand, and R3 and R4, on the other hand, possibly forming with the nitrogen atom an n-membered ring (n between 3 and 8) optionally containing one or more heteroatoms chosen from N, O and S and possibly being substituted by one or more of the following groups: amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R5 and R6 are independently chosen from the following groups:

H (C1-C20)alkyl optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl, (C2-C20)alkenyl optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl, (C2-C20)alkynyl optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl, (C3-C8)cycloalkyl optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl, hetero(C3-C8)cycloalkyl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl, (C6-C14)aryl optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl, (C1-C13)heteroaryl bearing one or more heteroatoms chosen from N, O and S and optionally substituted by amino, hydroxyl, thio, halogen, (C1-C5)-alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C6-C14)aryl(C1-C5)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R5 and R6 possibly forming with the carbon atom to which they are attached an m-membered ring (m between 3 and 8) optionally containing one or more heteroatoms chosen from N, O and S and possibly being substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, or possibly forming with the carbon atom a C10-C30 polycyclic residue optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)-alkoxy, cyano, trifluoromethyl, carboxyl, carboxymethyl or carboxyethyl, R5 and R6 together also possibly representing the group =O or =S, the nitrogen atom of a heterocycloalkyl or heteroaryl group possibly being substituted by a (C1-C5)alkyl, (C3-C8)cycloalkyl, (C6-C14)aryl, (C6-C14)aryl(C1-C5) alkyl or (C1-C6)acyl group, and also the racemic forms, tautomers, enantiomers, diastereoisomers, epimers and mixtures thereof, and the pharmaceutically acceptable salts.

One particular group of the invention concerns the pharmaceutical compositions according to the invention in which the triazine derivatives are compounds of the formula (I) in which R5 is hydrogen.

Another particular group of the invention concerns the pharmaceutical compositions according to the invention in which the triazine derivatives are compounds of the formula (I) in which R5 and R6 form with the carbon atom to which they are attached an m-membered ring (m between 3 and 8) optionally containing one or more heteroatoms chosen from N, O and S and possibly being substituted by one or more of the following groups: (C1-C5)alkyl, amino, hydroxyl, (C1-C5)alkylamino, alkoxy(C1-C5), (C1-C5)alkylthio, (C6-C14) aryl, is (C6-C14)aryl(C1-C5)alkoxy, or form with the carbon atom a C10-C30 polycyclic residue optionally substituted by amino, hydroxyl, thio, halogen, (C1-C5)alkyl, (C1-C5)alkoxy, (C1-C5)alkylthio, (C1-C5) alkylamino, (C6-C14)aryloxy, (C6-C14)aryl(C1-C5)-alkoxy, cyano, trifluoromethyl, carboxyl, carboxymethyl or carboxyethyl.

Another particular group of the invention concerns the pharmaceutical compositions according to the invention in which the triazine derivatives are compounds of the formula (I) in which R5 and R6 are independently chosen from the following groups:

(C1-C20)alkyl groups optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl.

Preferably, R1, R2, R3 and R4 are independently chosen from H and (C1-C20)alkyl groups optionally substituted by halogen, (C1-C5)alkyl, (C1-C5)alkoxy or (C3-C8)cycloalkyl; more preferably, R1=R2=H and R3=R4=(C1-C20) alkyl optionally substituted by halogen, (C1-C5)alkyl, (C1-C5)alkoxy, (C3-C8)cycloalkyl or vice versa.

Preferably, R5 and R6 are independently chosen from H and (C1-C20)alkyl groups optionally substituted by amino, hydroxyl, thio, halogen, (C1-C5)alkyl, (C1-C5)alkoxy, (C1-C5)alkylthio, (C1-C5)alkylamino, (C6-C14)-aryloxy, (C6-C14)aryl(C1-C5)alkoxy, cyano, trifluoromethyl, carboxyl, carboxymethyl or carboxyethyl; more preferably, R5=H and R6=(C1-C20)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)-alkoxy, cyano, trifluoromethyl, carboxyl, carboxymethyl or carboxyethyl or vice versa.

A more particular group of the invention concerns the pharmaceutical compositions according to the invention in which the triazine derivatives are compounds of the formula (I) in which R1 and R2 are a methyl group and R3 and R4 represent a hydrogen.

The term "m-membered ring formed by R5 and R6" in particular means a is saturated ring, such as a cyclohexyl, piperidyl or tetrahydropyranyl group.

The term "polycyclic group formed by R5 and R6" means an optionally substituted carbon-based polycyclic group and in particular a steroid residue.

Compounds of the formula (I) that may especially be mentioned include:

| | Formula | Salt |
|---|---|---|
| 1 | ![structure 1] | HCl |
| 2 | ![structure 2] | HCl |
| 3 | ![structure 3] | |
| 4 | ![structure 4] | HCl |
| 5 | ![structure 5] | Methane-sulfonate |
| 6 | ![structure 6] | |
| 7 | ![structure 7] | HCl |

-continued

| | Formula | Salt |
|---|---|---|
| 8 | 2-(dimethylamino)-4-(allylamino)-6,6-dimethyl-dihydrotriazine | HCl |
| 9 | 2-(dimethylamino)-4-(isopropylamino)-6,6-dimethyl-dihydrotriazine | HCl |
| 10 | 2-(dimethylamino)-4-amino-6-phenyl-dihydrotriazine | HCl |
| 11 | 2-(dimethylamino)-4-amino-6-(4-methoxyphenyl)-dihydrotriazine | HCl |
| 12 | 2-(dimethylamino)-4-amino-6-(4-hydroxyphenyl)-dihydrotriazine | HCl |

-continued

| | Formula | Salt |
|---|---|---|
| 13 | 6-(4-hydroxyphenyl)-N2,N2,N4-trimethyl-1,6-dihydro-1,3,5-triazine-2,4-diamine | |
| 14 | N2-ethyl-N4,N4,6,6-tetramethyl-1,6-dihydro-1,3,5-triazine-2,4-diamine | Fumarate |
| 15 | N2,N2,N4,N4,6,6-hexamethyl-1,6-dihydro-1,3,5-triazine-2,4-diamine | HCl |
| 16 | N2,N2,N4,6,6-pentamethyl-1,6-dihydro-1,3,5-triazine-2,4-diamine | HCl |
| 17 | N,N,4,4-tetramethyl-6-(pyrrolidin-1-yl)-1,6-dihydro-1,3,5-triazin-2-amine | HCl |
| 18 | N2,N2,6-trimethyl-1,6-dihydro-1,3,5-triazine-2,4-diamine | HCl |

-continued

| | Formula | Salt |
|---|---|---|
| 19 | | HCl |
| 20 | | Carbonate |
| 21 | | Carbonate |
| 22 | | HCl |
| 23 | | HCl |
| 24 | | HCl |

-continued

| | Formula | Salt |
|---|---|---|
| 25 | | HCl |
| 26 | | HCl |
| 27 | | HCl |
| 28 | | HCl |
| 29 | | Carbonate |

-continued

| | Formula | Salt |
|---|---|---|
| 30 | [structure: 1,3,5-triazine ring with N(CH3)2, NH2, and two ethyl groups at 6-position] | Carbonate |
| 31 | [structure: spiro cyclopentane triazine with N(CH3)2 and NH2] | HCl |
| 32 | [structure: triazine with N(CH3)2, NH2, and n-propyl at 6-position] | Carbonate |
| 33 | [structure: triazine with N(CH3)2, NH2, unsubstituted CH2 at 6-position] | HCl |
| 34 | [structure: triazine with N(CH3)2, NH2, and cyclohexyl at 6-position] | para-Toluene-sulfonate |
| 35 | [structure: triazine with N(CH3)2, NH2, and gem-dimethyl at 6-position] | HCl |
| 36 | [structure: triazine with N(CH3)2, NH2, and CF3 at 6-position] | para-Toluene-sulfonate |

-continued

| | Formula | Salt |
|---|---|---|
| 37 | [structure: 6-benzyl-N,N-dimethyl-1,6-dihydro-1,3,5-triazine-2,4-diamine] | para-Toluene-sulfonate |
| 38 | [structure: dimethylamino-amino dihydrotriazine spiro-tetrahydropyran] | HCl |
| 39 | [structure: dimethylamino-amino dihydrotriazine spiro-(N-methyl)piperidine] | HCl |
| 40 | [structure: 6-(2-furyl)-N,N-dimethyl-1,6-dihydro-1,3,5-triazine-2,4-diamine] | HCl |
| 41 | [structure: 6-(phenoxymethyl)-N,N-dimethyl-1,6-dihydro-1,3,5-triazine-2,4-diamine] | para-Toluene-sulfonate |
| 42 | [structure: 6-tert-butyl-N,N-dimethyl-1,6-dihydro-1,3,5-triazine-2,4-diamine] | HCl |

-continued

| | Formula | Salt |
|---|---|---|
| 43 | 2-(dimethylamino)-4-amino-6-isobutyl-dihydrotriazine | HCl |
| 44 | 2-(dimethylamino)-4-amino-6-isopropyl-dihydrotriazine | HCl |
| 45 | 2-(dimethylamino)-4-amino-6-(cyclohex-3-enyl)-dihydrotriazine | para-Toluene-sulfonate | and more preferably the compound of Example 18.

According to yet another preferred embodiment, the invention more particularly relates to pharmaceutical compositions chosen from:

(+)-2-amino-3,6-dihydro-4-dimethylamino-6-methyl-1,3,5-triazine hydrochloride, and rosiglitazone;

(+)-2-amino-3,6-dihydro-4-dimethylamino-6-methyl-1,3,5-triazine hydrochloride, and troglitazone;

(+)-2-amino-3,6-dihydro-4-dimethylamino-6-methyl-1,3,5-triazine hydrochloride, and pioglitazone;

(+)-2-amino-3,6-dihydro-4-dimethylamino-6-methyl-1,3,5-triazine hydrochloride, and muraglitazar.

The term "insulin sensitiser" means any compound capable of increasing the sensitivity of tissues to insulin. Insulin sensitisers include, for example, tyrosine phosphatase inhibitors (PTP inhibitors), GSK-3 inhibitors, retinoid X receptor agonists (RXR agonists), glitazones (TZD), non-TZD PPARγ agonists, PPARα/PPARγ double agonists, agonists based on compounds containing vanadium, and biguanides, for instance metformin. Insulin sensitisers may also be in the form of pharmaceutically acceptable salts, such as, in a non-limiting manner, the hydrochloride, hydrobromide, hydroiodide, sulfate, nitrate, phosphate, citrate, methanesulfonate, trifluoroacetate or acetate, the sodium ion, the potassium ion, the calcium ion or the magnesium ion.

The term "glitazones" includes, in a non-limiting manner, englitazone, darglitazone, ciglitazone, DRF2189, BM-13.1246, AY-31637, YM268, AD-5075, DN-108, rosiglitazone, pioglitazone, troglitazone, MCC555, T-174 and KRP297.

The term "non-TZD PPARγ agonist" more particularly includes N-(2-benzoylphenyl)-L-tyrosine analogues, such as, in a non-limiting manner, GI-262570 and JTT501.

The term "PPARα/PPARγ double agonist" includes, in a non-limiting manner, compounds, such as: NNC-61-4655, TZD18, LY-510929, LY-465608, LSN862, GW-409544, Muraglitazar, Ragaglitazar, Tesaglitazar, and also the compounds described in WO 03/011819 (Example 8) and WO 00/039113 (Example 16 b describing oxeglitazar).

The compounds of the invention of the formula (I) as defined above, containing a sufficiently basic function, or both, may include the corresponding pharmaceutically acceptable salts of organic or mineral acids.

For the purposes of the present invention, the term "corresponding pharmaceutically acceptable salts of organic or mineral acids" means any salt prepared from any non-toxic pharmaceutically acceptable organic or inorganic acid. Such acids include acetic acid, benzenesulfonic acid, benzoic acid, citric acid, carbonic acid, ethanesulfonic acid, fumaric acid, gluconic acid, glutamic acid, hydrobromic acid, hydrochloric acid, lactic acid, mandelic acid, malic acid, maleic acid, methanesulfonic acid, mucic acid, nitric acid, pamoic acid, pantothenic acid, phosphoric acid, succinic acid, tartaric acid and para-toluenesulfonic acid. Hydrochloric acid is advantageously used.

The invention also relates to the chiral salts of the compounds of the formula (I) used for the separation of the racemates of the compounds of the formula (I).

By way of example, the following chiral acids are used: (+)-D-di-O-benzoyltartaric acid, (−)-L-di-O-benzoyltartaric acid, (−)-L-di-O,O'-p-toluoyl-L-tartaric acid, (+)-D-di-O,O'- p-toluoyl-L-tartaric acid, (R)-(+)-malic acid, (S)-(−)-malic acid, (+)-camphanic acid, (−)-camphanic acid, R-(−)-1,1′-binaphthalen-2,2′-diylhydrogenophosphonic acid, (+)-camphoric acid, (−)-camphoric acid, (S)-(+)-2-phenylpropionic acid, (R)-(+)-2-phenylpropionic acid, D-(−)-mandelic acid, L-(+)-mandelic acid, D-tartaric acid, L-tartaric acid, or a mixture of two or more thereof.

The compounds of the formula (I) above also include the prodrugs of these compounds.

The term "prodrugs" means compounds which, when administered to the patient, are chemically and/or biologically converted in the live body into compounds of the formula (I).

In the present description, the terms used have, unless otherwise indicated, the following meanings:
the term "(C1-C20)alkyl" denotes a linear or branched alkyl radical containing from 1 to 20 carbon atoms. Among the C1-C20 alkyl radicals that may especially be mentioned, in a non-limiting manner, are methyl, ethyl, propyl, isopropyl, butyl, sec-butyl, tert-butyl, pentyl, hexyl, octyl, decyl, dodecyl, hexadecyl and octadecyl radicals;
the term "(C1-C20)alkenyl" denotes a linear or branched hydrocarbon-based radical containing one or more unsaturations in double bond form. As is alkylene radicals containing from 1 to 20 carbon atoms, mention may be made, in a non-limiting manner, of ethenyl, prop-2-enyl, but-2-enyl, but-3-enyl, pent-2-enyl, pent-3-enyl and pent-4-enyl radicals;
the term "(C1-C20)alkynyl" denotes a linear or branched hydrocarbon-based radical containing one or more unsaturations in triple bond form. As alkylene radicals containing from 1 to 20 carbon atoms, mention may be made, in a non-limiting manner, of ethynyl, prop-2-ynyl, but-2-ynyl, but-3-ynyl, pent-2-ynyl, pent-3-ynyl and pent-4-ynyl radicals;
the term "alkoxy" refers to the term "alkyl-oxy";
the term "halogen" refers, in a non-limiting manner, to fluorine, chlorine or bromine;
the term "(C6-C14)aryl(C1-C20)alkyl" refers to the corresponding -alkylaryl groups. Mention will be made in particular of benzyl and phenethyl groups;
the term "(C6-C14)aryl" refers to an aromatic group containing from 6 to 14 carbon atoms with at least one of the rings having a system of conjugated pi electrons, and including biaryls, which may be optionally substituted. Mention will be made in particular of biphenyl, phenyl, naphthyl, anthryl and phenanthryl radicals;
the term "hetero(C6-C14)aryl" refers to a 6-14-membered aromatic heterocycle containing 1-4 heteroatoms, the other atoms being carbon atoms. Among the heteroatoms, mention will be made in particular of oxygen, sulfur and nitrogen. Among the heteroaryl radicals, mention will be made more particularly of furyl, thienyl, pyridyl, pyrrolyl, pyrimidyl, pyrazinyl, oxazolyl, oxadiazolyl, isoxazolyl, quinolyl and thiazolyl radicals;
the term "(C3-C8)cycloalkyl" refers to a saturated hydrocarbon-based ring and containing monocyclic, bicyclic and polycyclic radicals containing from 3 to 8 carbon atoms. Mention will be made, in a non-limiting manner, of cyclopropyl and cyclobutyl radicals.

It will be appreciated that the compounds that are useful according to the present invention may contain asymmetric centres. These asymmetric centres may be, independently, in R or S configuration. It will be clear to a person skilled in the art that certain compounds that are useful according to the invention may also exhibit geometrical isomerism. It should be understood that the present invention includes individual geometrical isomers and stereoisomers and mixtures thereof, including racemic mixtures, of compounds of the formula (I) above. Isomers of this type can be separated from mixtures thereof by application or adaptation of known processes, for example chromatography techniques or recrystallisation techniques, or they are prepared separately from suitable isomers of their intermediates.

The enantiomers of the compounds according to the invention and the process for the preparation of them are especially described in patent application WO 2004/089917, the content of which is incorporated herein by reference.

The present patent application also concerns the polymorphic forms of the compounds, as obtained according to patent application WO 2004/089917, for instance the A1 polymorphic form of the salt (+)-2-amino-3,6-dihydro-4-dimethylamino-6-methyl-1,3,5-triazine hydrochloride.

The present invention also relates to the other polymorphic forms of the compounds, such as the H1 polymorphic form of the salt (+)-2-amino-3,6-dihydro-4-dimethylamino-6-methyl-1,3,5-triazine hydrochloride, which can be prepared as follows:

Approximately 3 g of the A1 form of Example 18 are dissolved in 50 ml of 1 mol/l HCl at room temperature. The clear solution obtained is left to evaporate at room temperature, in an open beaker, until a solid residue crystallises.

The Characterisation is Performed by:
FT-IR Spectroscopy:
Brüker Vector 22
2 $cm^{-1}$ spectral resolution
32 scans
KBR discs (analogous to method A AA21505)
To evaluate the intensity of the IR bands, the IR spectra were normalised by vectorisation in the spectral range 4000-400 $cm^{-1}$ as an absorption spectrum.
Preadjustment was Performed:
s: A>0.05
m: 0.01<A<0.05
w: A<0.01.
FT-Raman Spectroscopy:
Brüker RFS-100
excitation: 1064 nm
spectral resolution: 1 $cm^{-1}$
1000 mW
1000 scans
focalised
aluminium crucible (analogous to method RA AA21505)
To evaluate the intensity of the Raman bands, Raman spectra were normalised by vectorisation in the spectral range 3600-200 $cm^{-1}$. Preadjustment was performed:
s: A>0.05
m: 0.01<A<0.05
w: A<0.01
Powder X-Ray Diffraction (XRD)
diffractometer D5000 (Brüker AXS)
radiation CuKα1 at 1.5406 Å (U=30 kV, A=40 mA)
Transmission mode
Detector in sensitive position
Primary monochromator
Angle range: 3-65° 2θ
Stage width: 0.05° 2θ
Measuring time/stage: 1.4 s
The XRD machine is set at 2θ±0.1°.
Results
A1 Form:
XRD:

| No. | d[Å] | 2θ | I/Io |
|---|---|---|---|
| 1 | 5.98 | 14.8 | 85 |
| 2 | 5.26 | 16.8 | 83 |
| 3 | 4.35 | 20.4 | 30 |
| 4 | 3.57 | 24.9 | 100 |
| 5 | 3.50 | 25.4 | 53 |
| 6 | 3.36 | 26.5 | 96 |
| 7 | 3.31 | 26.9 | 52 |
| 8 | 3.04 | 29.3 | 57 |
| 9 | 2.90 | 30.8 | 30 |
| 10 | 2.74 | 32.7 | 35 |

FT-IR bands (in cm$^{-1}$):
3384+/−1.5 (m), 3199+/−1.5 (m), 3163+/−1.5 (m), 3107+/−1.5 (m), 2993+/−1.5 (m), 2983+/−1.5 (m), 1652+/−1.5 (s), 1606+/−1.5 (s), 1576+/−1.5 (s), 1557+/−1.5 (s), 1505+/−1.5 (s), 1449+/−1.5 (m), 1427+/−1.5 (m), 1405+/−1.5 (m), 1383+/−1.5 (m), 1348+/−1.5 (m), 1306+/−1.5 (m), 1263+/−1.5 (w), 1235+/−1.5 (w), 1185+/−1.5 (w), 1096+/−1.5 (w), 1068+/−1.5 (w), 980+/−1.5 (w), 946+/−1.5 (w), 868+/−1.5 (w), 761+/−1.5 (w), 687+/−1.5 (m), 655+/−1.5 (m), 558+/−1.5 (w), 521+/−1.5 (w), 478+/−1.5 (w)

FT-Raman bands (in cm$^{-1}$):
3217+/−1.5 (w), 2994+/−1.5 (m), 2983+/−1.5 (m), 2936+/−1.5 (s), 2883+/−1.5 (m), 1645+/−1.5 (w), 1602+/−1.5 (m), 1554+/−1.5 (m), 1453+/−1.5 (m), 1428+/−1.5 (m), 1349+/−1.5 (w), 1308+/−1.5 (w), 979+/−1.5 (m), 866+/−1.5 (w), 761+/−1.5 (w), 686+/−1.5 (s), 583+/−1.5 (m), 555+/−1.5 (s), 525+/−1.5 (m), 479+/−1.5 (m), 410+/−1.5 (m), 401+/−1.5 (m), 307+/−1.5 (m)

H1 Form
XRD:

| No. | d[Å] | 2θ | I/Io |
|---|---|---|---|
| 1 | 8.03 | 11.0 | 69 |
| 2 | 7.27 | 12.2 | 25 |
| 3 | 6.11 | 14.5 | 24 |
| 4 | 4.01 | 22.1 | 86 |
| 5 | 3.64 | 24.5 | 100 |
| 6 | 3.26 | 27.3 | 51 |
| 7 | 3.08 | 29.0 | 29 |
| 8 | 3.04 | 29.4 | 34 |
| 9 | 2.82 | 31.7 | 61 |
| 10 | 2.66 | 33.6 | 26 |

FT-IR bands (in cm$^{-1}$):
3386+/−1.5 (m), 3080+/−3 (m), 1706+/−1.5 (s), 1691+/−1.5 (s), 1634+/−1.5 (m), 1513+/−1.5 (m), 1445+/−1.5 (w), 1241+/−1.5 (w), 1079+/−1.5 (w), 989+/−1.5 (w), 940+/−1.5 (w), 861+/−1.5 (w), 823+/−1.5 (w), 675+/−1.5 (w), 603+/−1.5 (w), 573+/−1.5 (w), 549+/−1.5 (w), 527+/−1.5 (w)

For the purposes of this text, it is understood that the tautomeric forms are included in the mention of a given group, for example thio/mercapto or oxo/hydroxy.

The pharmaceutical compositions according to the present invention are useful in the treatment of pathologies associated with insulin resistance syndrome (syndrome X).

Insulin resistance is characterised by a reduction in the action of insulin (cf. Presse Médicale, 1997, 26 (No. 14), 671-677) and is involved in a large number of pathological conditions, such as diabetes and more particularly non-insulin-dependent diabetes (type II diabetes or NIDDM), dyslipidaemia, obesity and arterial hypertension, and also certain microvascular and macrovascular complications, for instance atherosclerosis, retinopathy and neuropathy.

In this respect, reference will be made, for example, to Diabetes, vol. 37, 1988, 1595-1607; *Journal of Diabetes and its Complications*, 1998, 12, 110-119 or *Horm. Res.*, 1992, 38, 28-32.

The aim of the present invention is to propose a pharmaceutical composition for significantly improving the condition of diabetics.

The pharmaceutical compositions of the invention especially have hypoglycaemiant activity.

The compounds of the formula (I) are therefore useful in the treatment of is pathologies associated with hyperglycaemia.

The pharmaceutical composition comprising the triazine compound of the formula (I) in combination with an insulin sensitiser can be prepared by mixing together the various active principles, either all together or independently with a physiologically acceptable support, an excipient, a binder, a diluent, etc. It is then administered orally or non-orally, for instance via the parenteral, intravenous, cutaneous, nasal or rectal route. If the active principles are formulated independently, the corresponding formulations can be mixed together extemporaneously using a diluent and are then administered or can be administered independently of each other, either successively or sequentially.

The pharmaceutical compositions of the invention include formulations, such as granules, powders, tablets, gel capsules, syrups, emulsions and suspensions, and also forms used for non-oral administration, for instance injections, sprays or suppositories.

The pharmaceutical forms can be prepared via the known conventional techniques.

The preparation of an orally administered solid pharmaceutical form will be performed by the following process: an excipient (for example lactose, sucrose, starch, mannitol, etc.), a disintegrant (for example calcium carbonate, calcium carboxymethylcellulose, alginic acid, sodium carboxymethylcellulose, colloidal silicon dioxide, sodium croscarmellose, Crospovidone, guar gum, magnesium aluminium silicate, microcrystalline cellulose, cellulose powder, pregelatinised starch, sodium alginate, starch glycolate, etc.), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose, guar gum, etc.) and a lubricant (for example talc, magnesium stearate, polyethylene 6000, etc.) are, for example, added to the active principle(s) and the mixture obtained is then tableted. If necessary, the tablet can be coated via the known techniques, in order to mask the taste (for example with cocoa powder, mint, borneol, cinnamon powder, etc.) or to allow enteric dissolution or sustained release of the active principles. The coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide, quinoline yellow lake, etc.). Pharmaceutical forms, such as tablets, powders, sachets and gel capsules can be used for an oral administration.

The liquid pharmaceutical forms for oral administration include solutions, suspensions and emulsions. The aqueous solutions can be obtained by dissolving the active principles in water, followed by addition of flavourings, colorants, stabilisers and thickener, if necessary. In order to improve the solubility, it is possible to add ethanol, propylene glycol or other pharmaceutically acceptable non-aqueous solvents. The aqueous suspensions for oral use can be obtained by dispersing the finely divided active principles in water with a viscous product, such as natural or synthetic gums, resins, methylcellulose or sodium carboxymethylcellulose.

The pharmaceutical forms for injection can be obtained, for example, by the following process. The active principle(s) is (are) dissolved, suspended or emulsified either in an aqueous medium (for example distilled water, physiological saline, Ringer's solution, etc.) or in an oily medium (for example a plant oil, such as olive oil, sesame seed oil, cottonseed oil, corn oil, etc., or propylene glycol), with a dispersant (for example Tween 80, HCO 60 (Nikko Chemicals), polyethylene glycol, carboxymethylcellulose, sodium alginate, etc.), a preserving agent (for example methyl p-hydroxybenzoate, propyl p-hydroxybenzoate, benzyl alcohol, chlorobutanol, phenol, etc.), an isotonicity agent (for example sodium chloride, glycerol, sorbitol, glucose, etc.) and also other additives, such as, if desired, a solubilising agent (for example sodium salicylate, sodium acetate, etc.) or a stabiliser (for example human serum albumin).

A pharmaceutical form for external use can be obtained from a solid, semi-solid or liquid composition containing the active principle(s). For example, to obtain a solid form, the active principle(s) is (are) treated, alone or as mixtures, with excipients (for example lactose, mannitol, starch, microcrystalline cellulose, sucrose, etc.) and a thickener (for example natural gums, cellulose is derivatives, acrylic polymers, etc.) so as to convert them into powder. The liquid pharmaceutical compositions are prepared in substantially the same way as the forms for injection, as indicated previously. The semi-solid pharmaceutical forms are preferably in the form of aqueous or oily gels or in the form of a pomade. These compositions may optionally contain a pH regulator (for example carbonic acid, phosphoric acid, citric acid, hydrochloric acid, sodium hydroxide, etc.) and a preserving agent (for example p-hydroxybenzoic acid esters, chlorobutanol, benzalkonium chloride, etc.) and also other additives.

The daily doses of the insulin sensitisers are between 0.5 mg and 50 mg.

More particularly, if, in the present invention, rosiglitazone is used, the daily dose is between 1 mg and 8 mg, more preferably 4 mg. If pioglitazone is used, the daily dose is between 15 mg and 45 mg. If muraglitazar is used, the daily dose is between 0.5 mg and 20 mg, preferably 5 mg.

The daily doses of the compounds of the formula (I) are between 200 mg and 2000 mg.

The relative proportion of the constituents of the pharmaceutical compositions of the present invention takes into account the recommended dosages of the respective active principles. These relative proportions of insulin sensitisers, or of pharmaceutically acceptable salts thereof, and of the compounds of the formula (I), or of pharmaceutically acceptable salts thereof, thus vary in consequence. Preferably, the weight ratio of insulin sensitiser to the compound of the formula (I) ranges between 1/2 and 1/2000, more particularly from 1/4 to 1/2000 and especially from 1/5 to 1/2000. The frequency of administration of the compounds of the invention is between 1 and 2 administrations per day. In the case where the doses of compounds of the formula (I) necessitate more than one daily administration, the amounts of insulin sensitisers and the insulin sensitiser/compound of the formula (I) ratios are adjusted in consequence.

The aim of the present invention is also to propose a method of treatment via co-administration of effective amounts of a compound of the formula (I) and of an insulin sensitiser, and also kits for allowing this co-administration.

The present invention also relates to kits that are suitable for the treatment by the methods described above. These kits comprise a composition containing the compound of the formula (I) in the dosages indicated above and is a second composition containing the insulin sensitisers in the dosages indicated above, for a simultaneous, separate or sequential administration, in effective amounts according to the invention.

The term "co-administration" means the simultaneous, separate or sequential administration of one or more compounds to the same patient, over a period that may be up to 2 hours or even up to 12 hours. For example, the term co-administration includes (1) a simultaneous administration of the two compounds, (2) an administration of the first, followed 2 hours later by the administration of the second compound, (3) an administration of the first, followed 12 hours later by the administration of the second compound.

The examples below of compositions according to the invention are given as non-limiting illustrations.

EXAMPLES

The amounts are expressed on a weight basis.

Formulation Example 1

(+)-2-amino-3,6-dihydro-4-dimethylamino-6-methyl-1,3, 5-triazine hydrochloride: 1000 mg
 rosiglitazone: 4 mg
 microcrystalline cellulose: 114 mg
 croscarmellose: 28 mg
 polyvinylpyrrolidone: 40 mg
 magnesium stearate: 14 mg
 Opadry: 24 mg Formulation Example 2

(+)-2-amino-3,6-dihydro-4-dimethylamino-6-methyl-1,3, 5-triazine hydrochloride: 1000 mg
 pioglitazone: 25 mg
 microcrystalline cellulose: 115.5 mg
 croscarmellose: 28 mg
 polyvinylpyrrolidone: 40 mg
 magnesium stearate: 9 mg
 Opadry®: 24 mg Formulation Example 3

(+)-2-amino-3,6-dihydro-4-dimethylamino-6-methyl-1,3, 5-triazine hydrochloride: 750 mg
 rosiglitazone: 2 mg
 microcrystalline cellulose: 110 mg
 croscarmellose: 21 mg
 polyvinylpyrrolidone: 30 mg
 magnesium stearate: 10.5 mg
 Opadry®: 18 mg Formulation Example 4

(+)-2-amino-3,6-dihydro-4-dimethylamino-6-methyl-1,3, 5-triazine hydrochloride: 1000 mg
 muraglitazar: 5 mg
 microcrystalline cellulose: 150 mg
 croscarmellose: 24 mg
 polyvinylpyrrolidone: 44 mg magnesium stearate: 8 mg Eudragit®: 24 mg Biological Test: Modulation of Glucose Levels with the Combinations of the Invention with Insulin Sensitisers The capacity of the compounds of the invention in combination with insulin-sensitising antidiabetic compounds to modify the blood glucose levels is evaluated in vivo in diabetic GK rats.

Alone or in combination, the antidiabetic agents are administered twice a day (bid) to the GK rats for 4 days. The oral glucose tolerance test (OGTT) is performed after the last day of treatment.

OGTT is performed in the morning after 3 hours of fasting by oral administration of a glucose charge of 2 g/kg of body mass. The blood samples are collected from the tail vein at 0; 10; 20; 30; 45; 60; 90 and 120 minutes to determine the glucose levels.

Results for the Combinations According to the Invention

The combination of rosiglitazone and of the hydrochloride salt of (+)-2-amino-3,6-dihydro-4-dimethylamino-6-methyl-1,3,5-triazine was tested as follows. The two compounds were administered alone and in combination. The doses used for the hydrochloride salt of (+)-2-amino-3,6-dihydro-4-dimethylamino-6-methyl-1,3,5-triazine were 50 and 100 mg/kg PO twice daily for 4 days. For rosiglitazone, the doses used were 1 and 5 mg/kg PO twice daily for 4 days. The following combination was tested:

the hydrochloride salt of (+)-2-amino-3,6-dihydro-4-dimethylamino-6-methyl-1,3,5-triazine: 100 mg/kg and rosiglitazone: 5 mg/kg PO twice daily for 4 days.

| Treatment | Glycaemia before treatment mmol/l | Glycaemia after 4 days of treatment mmol/l | % variation vs control | Glycaemia R under the curve (AUC) | % decrease in AUC vs control |
|---|---|---|---|---|---|
| Control GK n = 8 | 12.93 +/− 0.41 | 13.10 +/− 0.87 | | 3343 + 262 | |
| (+)-2-amino-3,6-dihydro-4-dimethylamino-6-methyl-1,3,5-triazine hydrochloride salt 100 mg/kg bid | 12.95 +/− 0.41 | 11.01 +/− 0.37 | −16% | 2688 +/− 99 | −19.6% |
| Rosiglitazone 5 mg/kg bid | 12.81 +/− 0.27 | 10.52 +/− 0.84 | −19.7% | 2954 +/− 150 | −11.6% |
| (+)-2-amino-3,6-dihydro-4-dimethylamino-6-methyl-1,3,5-triazine hydrochloride salt 100 mg/kg bid + Rosiglitazone 5 mg/kg bid | 12.86 +/− 0.52 | 10.03 +/− 0.35 | −23.4% | 2311 +/− 121 | −30.9% |

After four days of treatment (placebo), the glycaemia of the control GK diabetic rats was not modified or increased significantly. At doses of 5 mg/kg of rosiglitazone and 100 mg/kg of the hydrochloride salt of (+)-2-amino-3,6-dihydro-4-dimethylamino-6-methyl-1,3,5-triazine, these agents induced a decrease in the fasted plasmatic glucose level. However, better glucose tolerance was observed with the hydrochloride salt of (+)-2-amino-3,6-dihydro-4-dimethylamino-6-methyl-1,3,5-triazine than with rosiglitazone.

In combination, rosiglitazone 5 mg/kg and the hydrochloride salt of (+)-2-amino-3,6-dihydro-4-dimethylamino-6-methyl-1,3,5-triazine 100 mg/kg showed much better efficacy than each compound individually. The combination of an insulin sensitiser, such as rosiglitazone and of a compound, such as the hydrochloride salt of (+)-2-amino-3,6-dihydro-4-dimethylamino-6-methyl-1,3,5-triazine generates better activity on the glucose tolerance and the plasmatic glucose level of each than that of the compounds.

The invention claimed is:

1. A pharmaceutical composition comprising, as active principle:

i) an insulin sensitiser, wherein the insulin sensitiser is metformin, and ii) 2-amino-3,6-dihydro-4-dimethylamino-6-methyl-1,3,5-triazine, or a racemic form, tautomer, enantiomer, diastereoisomer, epimer or polymorph thereof, or a mixture thereof, or a pharmaceutically acceptable salt thereof, in combination with one or more pharmaceutically acceptable excipients.

2. The pharmaceutical composition according to claim 1, wherein the 2-amino-3,6-dihydro-4-dimethylamino-6-methyl-1,3,5-triazine is (−)-2-amino-3,6-dihydro-4-dimethylamino-6-methyl-1,3,5-triazine, or a pharmaceutically acceptable salt thereof.

3. The pharmaceutical composition according to claim 1, wherein the 2-amino-3,6-dihydro-4-dimethylamino-6-methyl-1,3,5-triazine is (+)-2-amino-3,6-dihydro-4-dimethylamino-6-methyl-1,3,5-triazine, or a pharmaceutically acceptable salt thereof.

4. The pharmaceutical composition according to claim 1, wherein the 2-amino-3,6-dihydro-4-dimethylamino-6-methyl-1,3,5-triazine is in the form of a hydrochloride salt.

5. The pharmaceutical composition according to claim 1, wherein the insulin sensitiser is in the form of a pharmaceutically acceptable salt.

6. The pharmaceutical composition according to claim 1, which contains between 0.5 mg and 50 mg of insulin sensitiser.

7. The pharmaceutical composition according to claim 1, wherein the composition contains between 200 mg and 2000 mg of 2-amino-3,6-dihydro-4-dimethylamino-6-methyl-1,3,5-triazine.

8. The pharmaceutical composition according to claim 1, wherein the weight ratio of insulin sensitiser to 2-amino-3,6-dihydro-4-dimethylamino-6-methyl-1,3,5-triazine is between 1/2 and 1/2000.

9. The pharmaceutical composition according to claim 1, which is suitable for oral administration, in which the pharmaceutical composition is a powder, a coated tablet, a gel capsule, a sachet, a solution, a suspension or an emulsion.

10. A method for the treatment of diabetes comprising administering to a subject in need thereof an effective amount of an insulin sensitiser in combination with 2-amino-3,6-dihydro-4-dimethylamino-6-methyl-1,3,5-triazine, wherein the insulin sensitiser is metformin.

11. The method according to claim 10, for the treatment of non-insulin-dependent diabetes.

12. A method for the treatment of at least one of the pathologies associated with insulin resistance syndrome, selected from the group consisting of dyslipidaemia, obesity, arterial hypertension, microvascular complications and macrovascular complications, comprising administering to a subject in need thereof an effective amount of an insulin sensitiser in combination with 2-amino-3,6-dihydro-4-dimethylamino-6-methyl-1,3,5-triazine, wherein the insulin sensitiser is metformin.

13. The method according to claim 10, wherein the weight ratio of insulin sensitiser to 2-amino-3,6-dihydro-4-dimethylamino-6-methyl-1,3,5-triazine is between 1/2 and 1/2000.

14. The method according to claim 10, wherein the administration of 2-amino-3,6-dihydro-4-dimethylamino-6-methyl-1,3,5-triazine and that of the insulin sensitiser are simultaneous.

15. A kit comprising 2-amino-3,6-dihydro-4-dimethylamino-6-methyl-1,3,5-triazine and an insulin sensitizer, for simultaneous administration, wherein the insulin sensitiser is metformin.

16. The method of claim 12, wherein the pathology treated is selected from the group consisting of atherosclerosis, retinopathy, nephropathy and neuropathy.

17. The pharmaceutical composition according to claim 1, which contains 2-amino-3,6-dihydro-4-dimethylamino-6-methyl-1,3,5-triazine or a pharmaceutically acceptable salt thereof.

18. The pharmaceutical composition according to claim 1, wherein the 2-amino-3,6-dihydro-4-dimethylamino-6-methyl-1,3,5-triazine is (+)-2-amino-3,6-dihydro-4-dimethylamino-6-methyl-1,3,5-triazine or its hydrochloride salt.

19. The method according to claim 10, wherein the 2-amino-3,6-dihydro-4-dimethylamino-6-methyl-1,3,5-triazine and the insulin sensitiser are together in a composition.

20. The method according to claim 12, wherein the 2-amino-3,6-dihydro-4-dimethylamino-6-methyl-1,3,5-triazine and the insulin sensitiser are together in a composition.

* * * * *